United States Patent

Meier et al.

Patent Number: 6,028,131
Date of Patent: Feb. 22, 2000

[54] ANTIOXIDANTS CONTAINING PHENOL GROUPS AND AROMATIC AMINE GROUPS

[75] Inventors: Hans-Rudolf Meier, Marly; Gerrit Knobloch, Magden, both of Switzerland

[73] Assignee: Ciba Specialty Chemicals Corporation, Tarrytown, N.Y.

[21] Appl. No.: 09/043,901

[22] PCT Filed: Oct. 7, 1996

[86] PCT No.: PCT/EP96/04352

§ 371 Date: Apr. 27, 1998

§ 102(e) Date: Apr. 27, 1998

[87] PCT Pub. No.: WO97/14678

PCT Pub. Date: Apr. 24, 1997

[30] Foreign Application Priority Data

Oct. 19, 1995 [CH] Switzerland ............ 02970/95

[51] Int. Cl.[7] .................. C07C 69/96; C07C 321/00; C07C 315/00; C08K 5/41

[52] U.S. Cl. .................. 524/171; 524/199; 524/217; 524/239; 524/240; 558/275; 560/11; 560/12; 560/15; 560/16; 560/29; 564/50; 564/162; 564/165; 564/182

[58] Field of Search .................. 524/171, 199, 524/217, 239, 240; 558/275; 564/50, 162, 165, 182; 560/11, 12, 15, 16

[56] References Cited

U.S. PATENT DOCUMENTS

| | | | |
|---|---|---|---|
| 3,975,414 | 8/1976 | Kline | 260/42.47 |
| 4,534,874 | 8/1985 | Steinberg et al. | |
| 4,633,016 | 12/1986 | Buysch et al. | |
| 4,727,105 | 2/1988 | Hopper | 524/217 |
| 4,759,862 | 7/1988 | Meier | |
| 4,857,572 | 8/1989 | Meier et al. | |
| 5,225,444 | 7/1993 | Mueller et al. | |
| 5,304,314 | 4/1994 | Hsu et al. | |

*Primary Examiner*—Veronica P. Hoke
*Attorney, Agent, or Firm*—Luther A. R. Hall

[57] ABSTRACT

The invention relates to compounds of the formula I

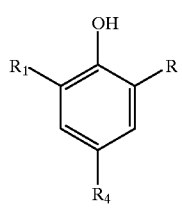

in which

R is $C_1$–$C_{18}$alkyl, $C_5$–$C_8$cycloalkyl, $C_7$–$C_9$phenylalkyl, —$CH_2$—A—$R_2$ or a group of the formula II,

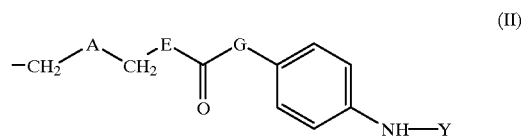

$R_1$ is $C_1$–$C_{18}$alkyl, $C_5$–$C_8$cycloalkyl, $C_7$–$C_9$phenylalkyl or a group of the formula (II), $R_2$ is $C_4$–$C_{18}$alkyl, —$(CH_2)_m$—$COOR_5$ or a group of the formula III,

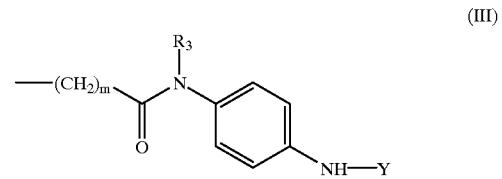

$R_3$ is hydrogen, $C_5$–$C_8$cycloalkyl or $C_1$–$C_{12}$alkyl, $R_4$ is $C_1$–$C_{18}$alkyl, $C_5$–$C_8$cycloalkyl, $C_7$–$C_9$phenylalkyl or a group of the formula II or IV,

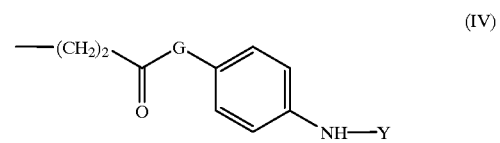

A is S or SO, E is a direct bond, —$CH_2$—, —$CH_2$—O— or —$CH_2$—NH—, G is —O— or —$NR_3$—, Y is $C_1$–$C_{18}$alkyl, cyclohexyl, phenyl or alpha- or beta-naphthyl, $R_5$ is $C_1$–$C_{18}$alkyl, and m is 1 or 2, with the provisos that either at least one of the radicals R and $R_4$ conforms to a group of the formula II or R is $CH_2$—A—$R_2$ and $R_4$ is a group of the formula IV.

The compounds are suitable for stabilizing organic material, in particular synthetic and natural rubber vulcanizates.

14 Claims, No Drawings

ANTIOXIDANTS CONTAINING PHENOL GROUPS AND AROMATIC AMINE GROUPS

The invention relates to compounds of the formula I described below, to compositions comprising these compounds, and to their use for stabilizing organic materials.

The stabilizers which have hitherto been incorporated into the molecular structure of the substrate to be stabilized are, for example, acrylates of the Ph—NH—$C_6H_4$—NH—CO—CH=$CH_2$ type. The double bond participates in the polymerization or crosslinking of the substrate (U.S. Pat. No. 3,975,414, U.S. Pat. No. 4,743,657; D. K. Parker and G. O. Schulz, Rubber Chemistry and Technology 62,732; D. E. Miller et al., Rubber World 1989, 200(5), 13–16 and 18–23; and CA 112:140956x). The advantage of such stabilizers which can be incorporated is that losses due to leaching-out or diffusion can be avoided. Stabilizers are already known, in particular for rubber, which conform to the formula

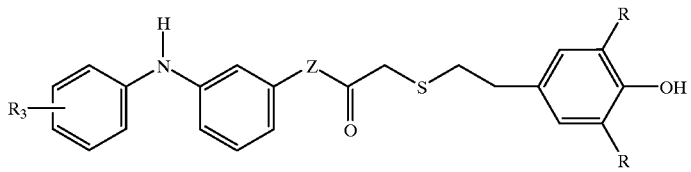

where Z is O or NH, X is $(C_2H_4OCH_2OC_2H_4SS)_m$ $C_2H_4OCH_2OC_2H_4$, R is t-$C_4$–$C_8$alkyl, m is from 4 to 24 and $R_3$ is H or $C_1$–$C_{18}$alkyl (U.S. Pat. No. 4,727,105).

The invention relates to compounds of the formula I

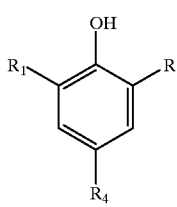

in which

R is $C_1$–$C_{18}$alkyl, $C_5$–$C_8$cycloalkyl, $C_7$–$C_9$phenylalkyl, —$CH_2$—A—$R_2$ or a group of the formula II,

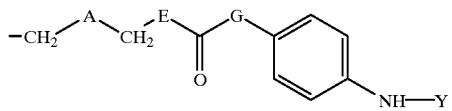

$R_1$ is $C_1$–$C_{18}$alkyl, $C_5$–$C_8$cycloalkyl, $C_7$–$C_9$phenylalkyl or a group of the formula (II), preferably methyl or tert-butyl, $R_2$ is $C_4$–$C_{18}$alkyl, —$(CH_2)_m$—$COOR_5$ or a group of the formula III,

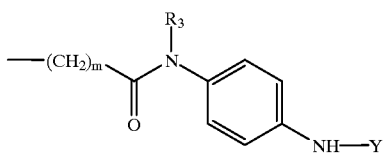

preferably $C_8$–$C_{12}$alkyl, $R_3$ is hydrogen, $C_5$–$C_8$cycloalkyl or $C_1$–$C_{12}$alkyl, preferably hydrogen, 2-propyl, 2-(4-methylpentyl), 2-(5-methylpentyl), 2-octyl, cyclohexyl or 3-(5-methylheptyl), in particular H, $R_4$ is $C_1$–$C_{18}$alkyl, $C_5$–$C_8$cycloalkyl, $C_7$–$C_9$phenylalkyl or a group of the formula II or IV,

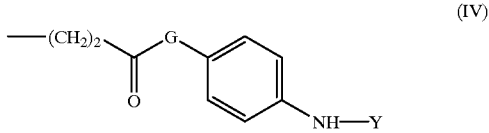

preferably methyl or t-butyl,

A is S or SO, preferably SO,

E is a direct bond, —$CH_2$—, —$CH_2$—O— or —$CH_2$—NH—, preferably a direct bond or —$CH_2$—, G is —O— or —$NR_3$—, preferably —$NR_3$—, Y is $C_1$–$C_{18}$alkyl, cyclohexyl, phenyl or alpha- or beta-naphthyl, preferably phenyl or alpha- or beta-naphthyl, $R_5$ is $C_1$–$C_{18}$alkyl, preferably $C_8$–$C_{13}$alkyl, and m is 1 or 2, preferably 2, with the provisos that either at least one of the radicals R and $R_4$ conforms to a group of the formula II or R is $CH_2$—A—$R_2$ and $R_4$ is a group of the formula IV, where some of these compounds, which can be used as antioxidants, can be chemically incorporated into certain substrates.

Preference is given to compounds of the formula I described above in which

R is $C_1$–$C_8$alkyl, cyclohexyl, benzyl, —$CH_2$—A—$R_2$ or a group of the formula II, $R_1$ is $C_1$–$C_8$alkyl, cyclohexyl, benzyl or a group of the formula II, $R_4$ is $C_1$–$C_{12}$alkyl, cyclohexyl, benzyl or a group of the formula II or IV, $R_2$ is $C_8$–$C_{12}$alkyl or —$(CH_2)_m$—$COOR_5$, $R_5$ is $C_8$–$C_{13}$alkyl, and E is a direct bond or —$CH_2$—.

Particular preference is given to compounds of the formula I described above in which R is $C_1$–$C_4$alkyl, —$CH_2$—A—$R_2$ or a group of the formula II, $R_1$ is $C_1$–$C_4$alkyl or a group of the formula II,
$R_4$ is $C_1$–$C_4$alkyl or a group of the formula II or IV,
$R_2$ is $C_8$–$C_{12}$alkyl,
$R_3$ is hydrogen, $C_1$–$C_8$alkyl or cyclohexyl,
E is a direct bond,
G is $NR_3$, and
Y is phenyl or alpha- or beta-naphthyl ($C_1$–$C_4$alkyl radicals here are preferably methyl or tert-butyl).

A is particularly preferably SO.

Preference is furthermore given to compounds of the formula I in which R is —$CH_2$—A—$R_2$, $R_1$ is $C_1$–$C_{18}$alkyl, $C_5$–$C_8$cycloalkyl or $C_7$–$C_9$phenylalkyl and $R_4$ is a group of the formula IV; or in which R is a group of the formula II and $R_1$ and $R_4$, independently of one another, are $C_1$–$C_{18}$alkyl, $C_5$–$C_8$cycloalkyl or $C_7$–$C_9$phenylalkyl; or in which $R_4$ is a group of the formula II and R and $R_1$, independently of one another, are $C_1$–$C_{18}$alkyl, $C_5$–$C_8$cycloalkyl or $C_7$–$C_9$phenylalkyl.

If the compounds of the formula I contain two or three groups of the formula ii or IV, the groups E in the formula II are preferably identical to one another.

Depending on the stated number of carbon atoms, alkyl is, for example, methyl, ethyl, n-propyl, isopropyl, n-, i-, sec- or t-butyl, pentyl, hexyl, heptyl, octyl, 2-ethylhexyl, i-octyl, decyl, nonyl, undecyl, dodecyl, tridecyl, quatrodecyl, quindecyl, sedecyl, heptadecyl or octadecyl.

$C_5$–$C_8$Cycloalkyl is, for example, cyclopentyl, cyclohexyl, cycloheptyl or cyclooctyl.

$C_7$–$C_9$Phenylalkyl is, for example, benzyl, 1- or 2-phenylethyl, 3-phenylpropyl, α,α-dimethylbenzyl or 2-phenylisopropyl, preferably benzyl.

The compounds of the formula I are suitable for stabilizing organic material, in particular polymers, specifically vulcanizates made from natural and/or synthetic rubber. As a consequence of their active groups, the compounds are effective as antioxidants both when incorporated and in free form. Complete incorporation is not necessarily desired. An incorporation rate of around 50% is frequently regarded as advantageous. The incorporation can take place via the SO group onto double bonds in the substrate. If A is sulfur, the incorporation can be preceded by oxidation by atmospheric oxygen. The incorporation into the substrate can also take place during use of the finished article at temperatures of, for example, around 80° C. In substrates which do not contain double bonds, the compounds of the formula I are in the form of conventional, admixed antioxidants.

The invention thus also relates to compositions comprising an organic material which is sensitive to oxidative, thermal and/or photoinduced degradation and at least one compound of the formula I.

Examples of organic materials to be stabilized are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for example of cyclopentene or norbornene; furthermore polyethylene (which may optionally be crosslinked), for example high density polyethylene (HDPE), low density polyethylene (LDPE), linear low density polyethylene (LLDPE), branched low density polyethylene (BLDPE).

Polyolefins, i.e. polymers of monoolefins exemplified in the preceding paragraph, in particular polyethylene and polypropylene, can be prepared by various processes, especially by the following methods:

a) free-radical polymerization (normally under high pressure and at elevated temperature)

b) catalytic polymerization using a catalyst that normally contains one or more metals of group IVb, Vb, VIb or VIII. These metals usually have one or more ligands, such as oxides, halides, alcoholates, esters, ethers, amines, alkyls, alkenyls and/or aryls that may be either π- or σ-coordinated. These metal complexes may be in the free form or fixed to supports, for example to activated magnesium chloride, titanium(III) chloride, alumina or silicon oxide. These catalysts may be soluble or insoluble in the polymerization medium. The catalysts can be active by themselves in the polymerization or further activators may be used, for example metal alkyls, metal hydrides, metal alkyl halides, metal alkyl oxides or metal alkyloxanes, the metals being elements of groups Ia, IIa and/or IIIa. The activators may be modified, for example, with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene-propylene copolymers, linear low density polyethylene (LLDPE) and mixtures thereof with low density polyethylene (LDPE), propylene-but-1-ene copolymers, propylene-isobutylene copolymers, ethylene-but-i-ene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide or ethylene-acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned under 1), for example polypropylene-ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers and alternating or random polyalkylene-carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene-butadiene, styrene-acrylonitrile, styrene-alkyl methacrylate, styrene-butadiene-alkyl acrylate, styrene-butadiene-alkyl methacrylate, styrene-maleic anhydride, styrene-acrylonitrile-methyl acrylate; high impact strength mixtures of styrene copolymers and another polymer, for example a polyacrylate, a diene polymer or an ethylene-propylene-diene terpolymer; and block copolymers of styrene such as styrene-butadiene-styrene, styrene-isoprene-styrene, styrene-ethylene-butylene-styrene or styrene-ethylene-propylene-styrene.

7. Graft copolymers of styrene or α-methylstyrene, for example styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), for example the copolymer mixtures known as ABS, MBS, ASA or AES polymers.

8. Halogen-containing polymers such as polychloroprene, chlorinated rubber, chlorinated or chlorosulfonated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride; and copolymers thereof such as vinyl chloride-vinylidene chloride, vinyl chloride-vinyl acetate or vinylidene chloride-vinyl acetate.

9. Polymers derived from α,β-unsaturated acids and derivatives thereof, such as polyacrylates and polymethacrylates, polymethyl methacrylates, polyacrylamides and polyacrylonitriles, impact-modified with butyl acrylate.

10. Copolymers of the monomers mentioned under 9) with one other or with other unsaturated monomers, for example acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallylmelamine; and their copolymers with olefins mentioned in point 1.

12. Homopolymers and copolymers of cyclic ethers, such as polyalkylene glycols, polyethylene oxide, polypropylene oxide or copolymers thereof with bisglycidyl ethers.

13. Polyacetals such as polyoxymethylene and those polyoxymethylenes which contain comonomers, for example ethylene oxide; polyacetals modified with thermoplastic polyurethanes, acrylates or MBS.

14. Polyphenylene oxides and sulfides, and mixtures thereof with styrene polymers or polyamides.

15. Polyurethanes derived from hydroxyl-terminated polyethers, polyesters and polybutadienes on the one hand and aliphatic or aromatic polyisocyanates on the other, and precursors thereof.

16. Polyamides and copolyamides derived from diamines and dicarboxylic acids and/or from aminocarboxylic acids or the corresponding lactams, such as polyamide 4, polyamide 6, polyamide 616, 6/10, 6/9, 6/12, 4/6, 12/12, polyamide 11, polyamide 12, aromatic polyamides starting from m-xylene, diamine and adipic acid; polyamides prepared from hexamethylenediamine and isophthalic and/or terephthalic acid and with or without an elastomer as modifier, for example poly-2,4,4-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; or with polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, such as polyethylene terephthalate, polybutylene terephthalate, poly-1,4-dimethylolcyclohexane terephthalate and polyhydroxybenzoates, and block polyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, urea or melamine on the other hand, such as phenol-formaldehyde resins, urea-formaldehyde resins and melamine-formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example from epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, e.g. from bisglycidyl ethers or from cycloaliphatic diepoxides.

27. Natural polymers such as cellulose, natural rubber, gelatin and chemically modified polymer-homologous derivatives thereof, for example cellulose acetates, cellulose propionates and cellulose butyrates, or the cellulose ethers such as methylcellulose; as well as rosins and derivatives.

28. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Aqueous emulsions of natural or synthetic rubbers, for example natural rubber latex or latices of carboxylated styrene-butadiene copolymers.

30. Natural and synthetic organic substances which constitute pure monomer compounds or mixtures thereof, for example mineral oils, animal or vegetable fats, oils and waxes, or oils, waxes and fats based on synthetic esters (e.g. phthalates, adipates, phosphates or trimellitates), and blends of synthetic esters with mineral oils in any desired ratios by weight, as are employed for example as spinning preparations, and the aqueous emulsions thereof.

Of these, preference is given to substances containing double bonds since this allows the advantage of chemical incorporation into the substrate to be utilized, in particular elastomers.

Examples of elastomers which can be present in the novel compositions are the following materials:

1. Polydienes, for example polybutadiene, polyisoprene and polychloroprene; block polymers, for example styrene-butadiene-styrene, styrene-isoprene-styrene and acrylonitrile-butadiene copolymers.

2. Copolymers of monoolefins and diolefins with one another or with other vinyl monomers, for example ethylene-alkyl acrylate copolymers, ethylene-alkyl methacrylate copolymers, ethylene-vinyl acetate copolymers and terpolymers of ethylene with propylene and a diene, such as hexadiene, dicyclopentadiene or ethylidenenorbornene.

3. Halogen-containing polymers, for example polychloroprene, chlorinated rubber, chlorinated or chlorosulfonated polyethylene, epichlorohydrin homopolymers and copolymers, chlorotrifluoroethylene copolymers, polymers of halogen-containing vinyl compounds, for example polyvinylidene chloride and polyvinylidene fluoride; and copolymers thereof, such as vinyl chloride-vinylidene chloride, vinyl chloride-vinyl acetate and vinylidene chloride-vinyl acetate.

4. Polyurethanes derived from polyethers, polyesters and polybutadiene containing terminal hydroxyl groups on the one hand and aliphatic or aromatic polyisocyanates on the other hand, and precursors thereof.

5. Natural rubber.

6. Mixtures (polyblends) of the abovementioned polymers.

7. Aqueous emulsions of natural or synthetic rubbers, for example natural rubber latex or latices of carboxylated styrene-butadiene copolymers.

These elastomers can, if desired, be in the form of latices and can be stabilized as such. It is also possible for vulcanizates to be stabilized.

Preference is given to compositions in which the elastomer is a polydiene, such as polybutadiene rubber.

The incorporation into the organic materials can take place, for example, by mixing-in the novel compounds or mixtures and, if desired, further additives by customary methods of the art. Polymers, in particular synthetic polymers, can be incorporated before or during shaping or by applying the dissolved or dispersed compounds to the polymers, if necessary with subsequent evaporation of the solvent. In the case of elastomers, these can also be stabilized as latices. A further, preferred way of using the novel compounds comprises addition thereof during the production of rubber mixtures together with the conventional other mixture constituents and ingredients by conventional techniques in, for example, Banbury mixers, on mixing rolls or in mixing extruders. In particular, the presence of the compounds of the formula I during the mixing process and during subsequent shaping and the crosslinking reaction (vulcanization to give the finished rubber article) and during use of the finished article produces a chemical linkage to the elastomer/polymer. This can be determined, for example, analytically from the higher residual content of additive—measured from residual nitrogen—compared with compounds which cannot be incorporated. The invention therefore relates in particular to compositions in which compounds of the formula I are incorporated into or chemically linked to an elastomer/polymer.

The novel compounds or mixtures can also be added to the plastics to be stabilized in the form of a masterbatch which comprises these compounds, for example, in a concentration of from 2.5 to 25% by weight.

The novel polymer compositions can be used in various forms or converted into various products, for example as (to) films, fibres, tapes, moulding compositions, profiles or as binders for paints, adhesives or adhesive cements.

In addition to the novel compounds or mixtures, the novel compositions, in particular if they comprise organic, preferably synthetic, polymers, can also comprise further conventional additives known to the person skilled in the art, for example:

1. Antioxidants 1.1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)-phenol, 2,4-dimethyl-6-(1'-methylheptadec-1'-yl)phenol, 2,4-dimethyl-6-(1'-methyl tridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecyl-thiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)4-nonylphenol], 2,2'-methylenebis[6-(α,α-dimethylbenzyl)4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl) dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)4-n-dodecylmercaptobutane, 1,1,5,5-tetra-(5-tert-butyl-4-hydroxy-2-methylphenyl)pentane.

1.7. O-, N- and S-benzyl compounds, for example 3,5,3', 5'-tetra-tert-butyl-4,4'-dihydroxydibenzyl ether, octadecyl 4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl) dithioterephthalate, bis(3,5-di-tert-butyl-4-hydroxybenzyl) sulfide, isooctyl 3,5-di-tert-butyl-4-hydroxybenzylmercaptoacetate.

1.8. Hydroxybenzylated malonates, for example dioctadecyl 2,2-bis(3,5-di-tert-butyl-2-hydroxybenzyl)malonate, dioctadecyl 2-(3-tert-butyl-4-hydroxy-5-methylbenzyl) malonate, di-dodecyl mercaptoethyl-2,2-bis(3,5-di-tert-butyl-4-hydroxybenzyl)malonate, di-[4-(1,1,3,3-tetramethylbutyl)phenyl] 2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.

1.11. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N, N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)hydrazine.

1.18. Dihydroquinoline derivatives, for example polymerized 2,2,4-trimethyl-1,2-dihydroquinoline. 1. 19. Diphenylamines and other diarylamine derivatives, for example di(octylphenyl)amine.

1.20. p-Phenylenediamines, for example N-phenyl-N'-isopropyl-p-phenylenediamine, N-phenyl-N'-(1,3-dimethylbutyl)-p-phenylenediamine and N,N'-diphenyl-p-phenylenediamine.

1.21. Further antioxidants, for example 2-mercapto-4(S)-methylbenzimidazole, 2-mercaptotoluimidazole, and their zinc salts.

1.22. Naphthylamines, for example N-phenyl-α-naphthylamine and N-phenyl-β-naphthylamine (PBNA).

2. UV-absorbers and light stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octoxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300;

$$[RCH_2CH_2COO(CH_2)_3]_{\overline{2}}$$

where R=3'-tert-butyl-4'-hydroxy-5'-2H-benzotriazol-2-ylphenyl.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-m ethyl-4,6-di-tert-butylphenyl 3,5-di-tert-butyl-4-hydroxybenzoate.

2.4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxycinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl 3,5-di-tert-butyl-4-hydroxybenzylmalonate, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decan-2, 4-dione, bis(1-octyloxy-2,2,6,6-tetramethylpiperidyl) sebacate, bis(1-octyloxy-2,2,6,6-tetra-methylpiperidyl) succinate, the condensate of N,N'bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-(1,2,2,6,6-pentamethyl-4-piperidyl)pyrrolidine-2,5-dione.

2.7. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy disubstituted oxanilides and mixtures of o- and p-ethoxy disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl),6-bis(2,4-dimethylphenyl)-1,3, 5-triazine, 2-(2,4-dihydroxyphenyl)4,6-bis(2,4-dimethylphenyl)-1,3,5-triazine, 2,4-bis(2-hydroxyl-propoxyphenyl)-6-(2,4-dimethylphenyl)-1,3,5-triazine, 2-(2-hydroxy-4-octyloxyphenyl)4,6-bis(4-methylphenyl)-1, 3,5-triazine, 2-(2-hydroxy-4-dodecyloxyphenyl),4,6-b is(2, 4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropoxy)phenyl]4,6-bis(2,4-dimethylphenyl)-1,3,5-triazine.

3. Metal deactivators, for example, N,N'-diphenyloxalamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2, 4-triazole, bis(benzylidene)oxalyl dihydrazide, oxanilide, isophthaloyl dihydrazide, sebacoyl bisphenylhydrazide, N,N-diacetyladipoyl-dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, bisisodecyloxypentaerythritol diphosphite, bis(2,4-di-tert-butyl-methylphenyl)pentaerythritol diphosphite, bis(2,4,6-tri-tert-butylphenyl)pentaerythritol dipnosphite, tristearyl sorbitol triphosphite, tetrakis(2,4-di-tert-butylphenyl) 4,4'-biphenylene diphosphonite, 6-isooctyloxy-2,4,8,1-tetra-tert-butyl-12H-dibenzo[d,g]-1,3,2-dioxaphosphocin, 6-fluoro-2, 4,8,10-tetra-tert-butyl-1,2-methyl-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, and potassium palmitate, antimony pyrocatecholate or tin pyrocatecholate.

8. Nucleating agents, for example 4-tert-butylbenzoic acid, adipic acid and diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

11. Benzofuranones and indolinones, for example those described in U.S. Pat. No. 4,325,863, U.S. Pat. No. 4,338, 244, U.S. Pat. No. 5,175,312, U.S. Pat. No. 5,216,052, U.S. Pat. No. 5,252,643, DE-A4 316 611, DE-A4 316 622, DE-A4 316 876, EP-A-0 589 839 or EP-A-0 591 102 or 3-[4-(2-acetoxyethoxy)phenyl]-5,7-di-tert-butylbenzofuran-2-one, 5,7-di-tert-butyl-3-[4-(2-stearoyloxyethoxy)-phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)5,7-di-tert-butyl-benzofuran-2-one, 3-(3,5-dimethyl-4-pivaloyloxyphenyl)-5,7-di-tert-butyl-benzofuran-2-one.

12. Crosslinking agents, for example organic peroxides, sulfur, sulfur-containing vulcanization accelerators, zinc oxide and vulcanization activators.

The compounds of the formula I can be prepared by or analogously to known processes.

Starting materials for A' (T=S) are the compounds of the formulae C and D:

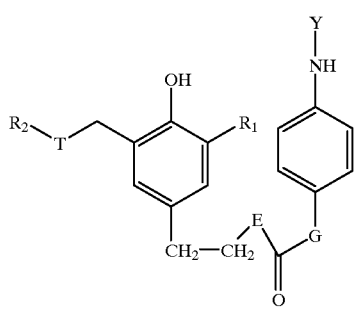

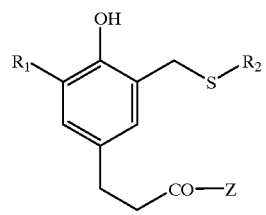

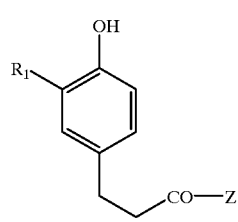

The methyl ester C (Z=OCH₃) is synthesized, for example, by the methods described in Patent Specifications U.S. Pat. No. 4,759,862 and U.S. Pat. No. 4,857,572 by thioalkylation of the corresponding, known 3'-substituted methyl 3-(4'-hydroxyphenyl)propionates D (for example methyl 3-(3'-t-butyl-4-hydroxyphenyl)propionate). The acid chloride C (Z=Cl) is prepared from the corresponding acid (Z=OH) by processes known from the literature.

Starting materials for B and B' are the compounds of the formulae E and E':

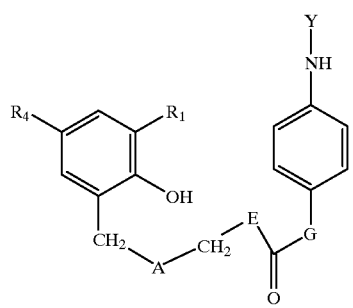

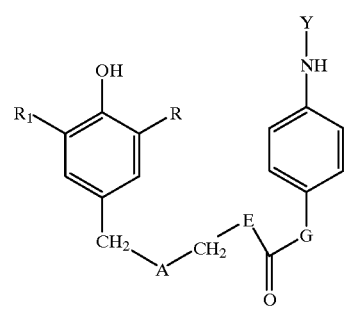

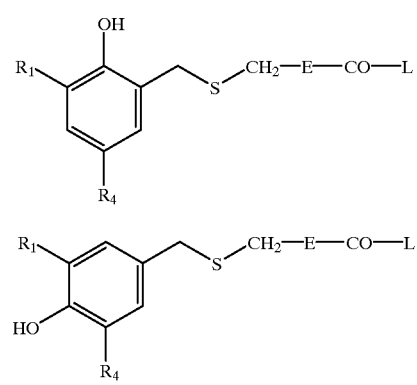

The methyl esters E and E' (L=OCH₃ and E=direct bond or —CH₂—) are synthesized, for example, analogously to the synthesis of C, starting from the corresponding 2,4- or 2,6-disubstituted phenols, formaldehyde and methyl thioglycolate or 3-thiopropionate. The compounds F and F' (Q=CH₂—O and CH₂—NH respectively)

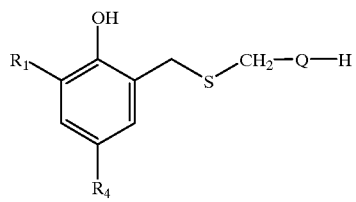

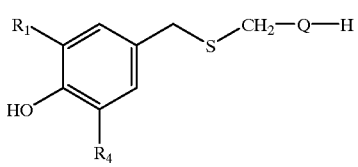

can be prepared analogously to the compounds described in U.S. Pat. No. 4,759,862 and U.S. Pat. No. 4,857,572.

a) Preparation of the compounds A' (T=SO), B and B' (A=SO)

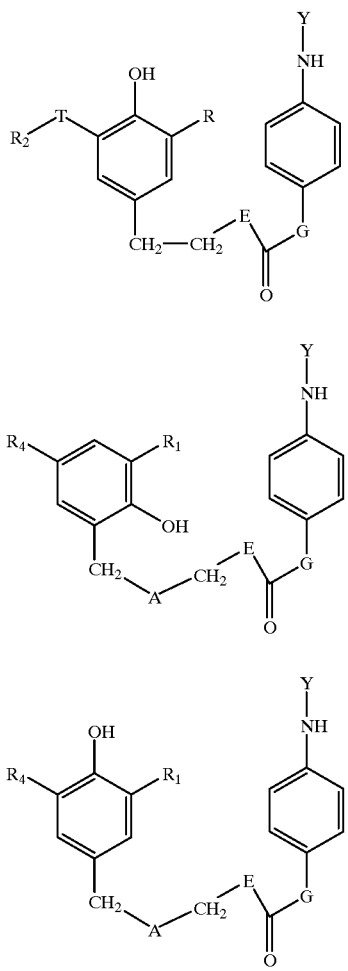

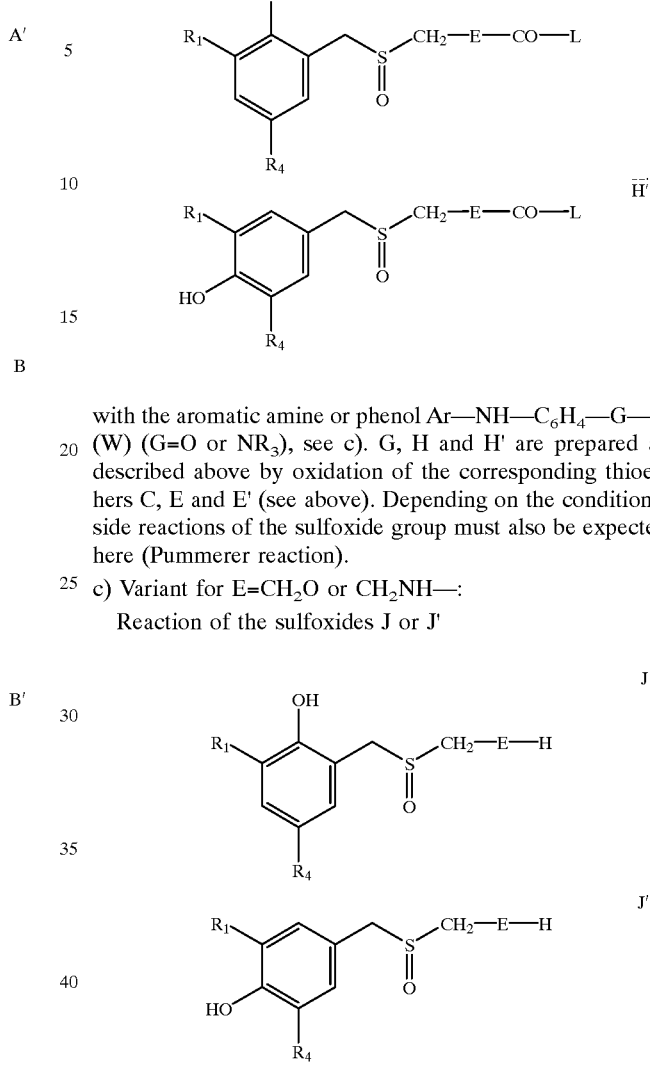

with the aromatic amine or phenol Ar—NH—C₆H₄—G—H (W) (G=O or NR₃), see c). G, H and H' are prepared as described above by oxidation of the corresponding thioethers C, E and E' (see above). Depending on the conditions, side reactions of the sulfoxide group must also be expected here (Pummerer reaction).

c) Variant for E=CH₂O or CH₂NH—:

Reaction of the sulfoxides J or J'

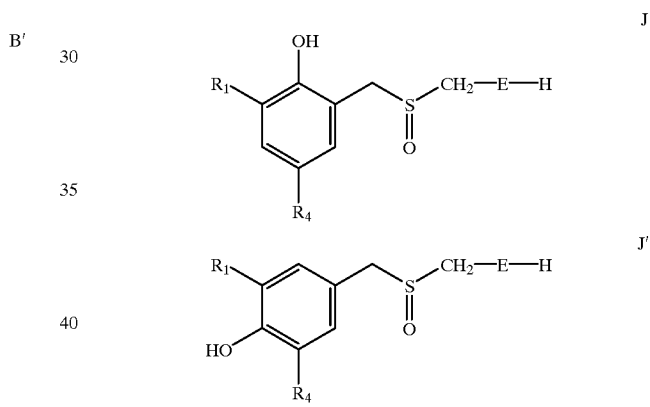

The sulfoxides A' (T=SO, E=direct bond), B and B' (A=SO) are prepared by oxidation of the corresponding thioethers A' (T=S), B and B' (A=S), as described in EP 473 549. Examples of oxidants which can be used are H₂O₂, t-butyl hydroperoxide and cumyl hydroperoxide. Suitable solvents are hydrocarbons, ethers and, for example, acetone.

b) Variant for E=direct bond or CH₂:

by reacting activated acid derivatives G, H and H'

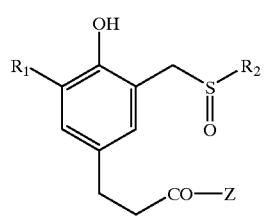

with the activated derivative aryl-NH—C₆H₄—NR₃—C(=O)—Q (W') (Q=halogen or another activating group).

d) Preparation of the compounds A', B and B' (A=S) where E=CH₂—O or CH₂NH

The urethanes or ureas B and B' (E=O or NH, G=NR₃) can be synthesized by reacting a compound aryl-NH—C₆H₄—NR₃—C(=O)—Q (W') (Q=halogen or another activating group) with the corresponding alcohol or amino derivative F or F' (E=CH₂—O or CH₂—NH).

e) Preparation of the compounds A, B and B' (A=S) where E=direct bond or CH₂

By substitution of a suitable [activated] acid derivative C, E or E' with an aromatic amine or phenol of the formula Ar—NH—C₆H₄—G—H (G=O or NR₃) (W), where Z is, inter alia, OCH₃, halogen or OH. The reaction is generally carried out without solvent or catalyst or in an inert solvent and/or using a catalyst or an auxiliary, which can be employed in a molar excess of up to five-fold. The reaction temperatures are in the range from 0° C. to 250° C. If Z=halogen, a tertiary amine is preferably used as acid scavenger.

In the case of polyfunctionalized compounds

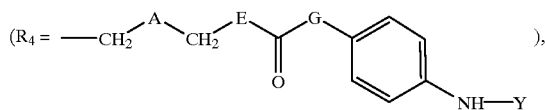

an at least two-fold molar excess of W or W' is used correspondingly.

The examples below serve to illustrate the invention in greater detail. In the examples and in the remainder of the description and in the claims, parts and percentages are by weight, unless stated otherwise.

EXAMPLE 1

Methyl 3-(3'-t-butyl-'-hydroxy-5-octylthiomethylphenyl)propionate 29.94 g (0.127 mol) of methyl 3-(3'-t-butyl-4-hydroxyphenyl)propionate, 20.39 g (0.139 mol) of octanethiol, 7.61 g (0.253 mol) of paraformaldehyde and 0.285 g of dimethylamine are refluxed for 15 hours in 30 ml of DMF. Evaporation of the solvent and dry ing at 60° C./0.015 mbar gives a yellow oil (51 g), which can be further purified by distillation (b.p. 80–90° C./0.06 mbar) and flash chromatography.

Analysis for $C_{23}H_{38}O_3S$: calc. C, 70.01; H, 9.71; S, 8.12%; found C, 69.92; H, 9.64; S, 8.15%

EXAMPLE 2

Methyl 3,5-di-t-butyl-2-hydroxybenzylthioacetate 50.96 g (0.247 mol) of 2,4-di-t-butylphenol, 28.84 g (0.272 mol) of methyl thioglycolate, 14.83 g (0.494 mol) of paraformaldehyde and 3.41 g of dimethylamine (33% in ethanol) are refluxed for 18 hours in 50 ml of DMF. The crude product (85.3 g) can, after working-up as described above, be further purified by flash chromatography. m.p. 55.0–55.5° C. Analysis for $C_{18}H_{28}SO_3$: calc. C, 66.63; H, 8.70; S 9.88%; found C 66.65; H 8.79; S 9.88%

EXAMPLE 3

3-(3'-t-Butyl-4'-hydroxy-5-octylthiomethylphenyl)-4'-phenylaminopropionanilide (compound of the formula I in which R is CH$_2$-S-n-octyl, R$_1$ is tert-butyl and R$_4$ is a group of the formula III where m=2, R$_3$=H and Y=phenyl)

20 g (50.7 mmol) of the compound from Example 1, 9.34 g (50.7 mmol) of 4-aminodiphenylamine and 50 mg of phenothiazine are heated at 180° C. for 2 hours. The brown, viscous crude product is purified by flash chromatography.

IR (KBr): 3375 and 3300 (OH and NH), 1654 (amide I), 1508 (aromatic), 1515 (amide II). Analysis for $C_{34}H_{46}N_2O_2S$: calc. C, 74.68; H, 8.48; N, 5.12; S, 5.86%; found C, 74,74; H, 8.67; N, 4.96; S, 5.65%.

EXAMPLE 4

3,5-Di-t-butyl-2-hydroxybenzylthio-4'-phenylaminoacetanilide (compound of the formula I in which R and R$_1$ are t-butyl and R$_4$ is a group of the formula II where A=S, E=direct bond, G=direct bond and Y=phenyl 34.03 g (0.105 mol) of the compound from Example 2 and 19.34 g (0.105 mol) of 4-aminodiphenylamine are heated at 180° C. for 8 hours. The brown, viscous crude product is purified by flash chromatography and recrystallization. Recrystallization from toluene/cyclohexane gives a crystalline product of m.p. 143.0–143.5° C.

Analysis for $C_{29}H_{36}N_2O_2S$: calc. C, 73.07; H, 7.61; N, 5.88; S, 6.73%; found C, 73.00; H, 7.63; N, 6.09; S, 6.67%.

EXAMPLE 5

3-(3'-t-Butyl-4'-hydroxy-5'-octylsulfinylmethylphenyl)-4'-phenylaminopropionanilide (compound from Example 3 where R=CH$_2$—SO-n-octyl)

4.5 g (8.23 mmol) of the compound from Example 3 are refluxed for 48 hours with 6.51 g (86.4 mmol) of 30% H$_2$O$_2$ in 40 ml of acetone.

The mixture is then diluted at 20–25° C. with 50 ml of hexane. Turbidity is removed by filtration. Evaporation of the filtrate gives 1.8 g of a pale brown crystalline product. Recrystallization from hexane/acetone at –20° C. gives 3.15 g of a white powder of m.p 114.5–116° C.

IR (KBr): 3300 (OH, NH), 1655 (amide I), 1597 (aromatic), 1514 (amide II). MS: 562. Analysis for $C_{34}H_{46}N_2O_3S$: calc. C, 72.56; H, 8.24; N, 4.98; S, 5.70%; found C, 72.14; H, 8.13; N, 4.60; S, 5,45%.

EXAMPLE 6

3,5-Di-t-butyl-2-hydroxybenzylsulfinyl-4'-phenylaminoacetanilide (compound from Example 4 where A=SO)

17.64 g (37 mmol) of the compound from Example 4 and 33.56 g (296 mmol) of 30% hydrogen peroxide are refluxed for 48 hours in 250 ml of methanol.

Work-up as in the above example and recrystallization from hexane/acetone give a yellowish powder of m.p. 134° C.

IR (KBr): 3300 (broad, NH, OH), 1652 (amide I), 1597 (aromatic), 1515 (amide I). MS: 492. (calc. for $C_{29}H_{36}N_2O_3S$: calc. C, 70.70; H, 7.37; N, 5.69; S, 6.51%; found C, 70.18; H, 7.27; N, 5.30; S, 6.16%.

EXAMPLE 7

Methyl 3,5-dimethyl-2-hydroxybenzylthioacetate[1] (intermediate)

Preparation analogous to Example 3 (using 3,5-dimethylphenol instead of 3,5-di-t-butylphenol). m.p. 47.047.5° C. Analysis for $C_{12}H_{16}SO_3$: calc. C, 59.98; H, 6.71; S, 13.34%; found C, 59.96; H, 6.73; S, 13.01%.

EXAMPLE 8

3,5-Dimethyl-2-hydroxybenzylthio-4'-phenylaminoacetanilide[2]

Preparation analogous to Example 4 using the compound described in Example 7. m.p. 137.5–138° C. (toluene). IR (KBr): 3335 (OH/NH), 1644 (amide I), 1593 (aromatic), 1514 (amide II). Analysis for $C_{23}H_{24}N_2O_2S$: calc. C, 70.38; H, 6.16; N, 7.14; S, 8.17%; found C, 69.90; H, 6.27; N, 7.07; S, 8.18%.

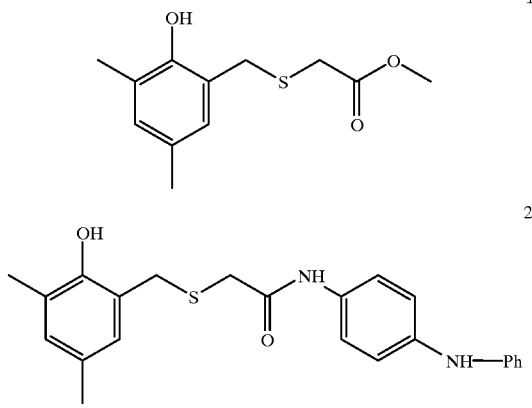

1

2

EXAMPLE 9

3,5-Dimethyl-2-hydroxybenzylsulfinyl-4'-phenylaminoacetanilide[3]

Preparation analogously to Example 6 from the compound described in Example 8. m.p. 176.5–177.5° C. (acetonitrile). IR (KBr): 3310 (OH/NH), 1653 (amide I), 1597 (aromatic), 1515 (amide II). Analysis for $C_{23}H_{24}N_2O_3S$: calc. C, 67.62; H, 5.92; N, 6.86; S, 7.85%; found C, 67.70; H, 5.91; N, 6.86; S, 7.69%.

EXAMPLE 10

Methyl 2-{3-t-butyl-4-hydroxy-5-([methoxycarbonylmethyl]thiomethyl)benzylthio}acetate[4] (intermediate)

Preparation from 274.6 g (2.587 mol) of methyl thioglycolate, 194.32 g (1.293 mol) of 2-t-butylphenol, 155.4 g (5.17 mol) of paraformaldehyde, 5.83 g of dimethylamine and 195 ml of DMF: the mixture of the above components is boiled for 3 hours under nitrogen in a flask fitted with mechanical stirrer and reflux condenser. The internal temperature is 110° C. The crude product is taken up in ethyl acetate and washed with 100 ml of water. Evaporation of the organic phase gives 476.7 g of a brown-red oil (95.3%). $^1$H NMR(CDCl$_3$): 7.15 and 6.95 (d, J=2.5Hz), 3.86 and 3.72 (2s, Ar—S—CH$_2$), 3.75 and 3.70 (2s, MeO), 3.16 and 3.08 (2s, CO—CH$_2$—S), 1.39 (t-butyl). Analysis for $C_{18}H_{26}S_2O_5$: calc. C 55.93; H 6.78; S 16.59%; found C 55.95; H 6.99; S 16.69%.

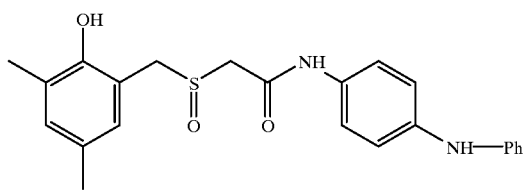

3

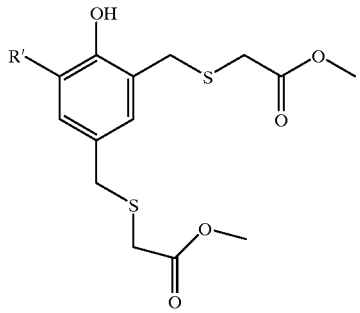

4

Examples 10 and 12
10: R' = t-Bu,
12: R' = Me,

EXAMPLE 11

2-{3-t-Butyl-4-hydroxy-5-[(2-oxo-2-(4-phenylaminophenyl)ethyl)thiomethyl]-benzylthio}(4-phenylaminophenyl)acetamide[5]

Preparation analogously to Example 3 from the dimethyl ester from Example 1.0 and two equivalents of 4-aminodiphenylamine.

M.p. 82–84° C. IR (KBr): 3375, 3323 (OH and NH); 1654 (amide I), 1597 (aromatic), 1515 (amide II). Analysis for $C_{40}H_{42}N_4O_3S_2$: calc. C, 69.54; H, 6.13; N, 8.11; S, 9.28%; found C, 70.08; H, 6.44; N, 8.08; S, 8.90%.

EXAMPLE 12

Methyl 2-{3-methyl-4-hydroxy-5-([methoxycarbonylmethyl]thiomethyl)benzylthio}acetate[4] (intermediate)

Preparation analogously to Example 10 using o-cresol. m.p. 63.1–64.5° C. (toluene), IR (film): 1732 (C=O, ester). Analysis for $C_{15}H_{20}S_2O_5$: calc. C, 52.31; H, 5.85; S, 18.62%; found C, 52.49; H, 5.95; S, 18.58%.

EXAMPLE 13

2-{3-methyl-4-hydroxy-5-[(2-oxo-2-(4-phenylaminophenyl)ethyl)thiomethyl]-benzylthio}-N-(4-phenylaminophenyl)acetamide[5]

Preparation analogously to Example 11. m.p. 133.5–134.5° C. (acetonitrile). IR (film) 3310 (NH, OH), 1654 (amide I), 1597 (aromatic), 1516 (amide II).

Analysis for $C_{37}H_{36}N_4O_3S_2$: calc. C, 68.49; H, 5.59; N, 8.64; S, 9.88%; found C, 68.43; H, 5.64; N, 8.64; S, 9.79%.

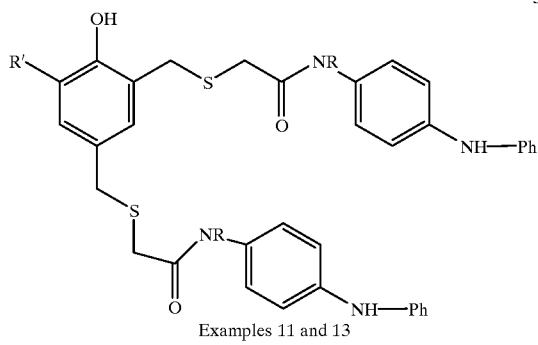

Examples 11 and 13
11: R' = t-Bu, R = H
13: R' = Me, R = H

EXAMPLE 14

Methyl 3-(3'-t-butyl-4'-hydroxy-5'-(methoxycarbonylmethyl)thiomethylphenyl) propionate[6]

Preparation analogously to Example 1; viscous, colourless oil. IR (film): 1730 (C=O, ester).

Analysis for $C_{17}H_{26}O_5S$: calc. C, 52.31; H, 5.85; S, 18.62%; found C, 52.49; H, 5.95; S, 18.58%.

EXAMPLE 15

3-{3-Methyl-4-hydroxy-5-[(2-oxo-2-(4-phenylaminophenyl)ethyl)thiomethyl]}-4-phenylaminopropionanilide[7]

Preparation analogously to Example 11; m p. 168° C. (toluene/acetone), IR (KBr): 3318 (OH), 1653 (amide I), 1597 (aromatic), 1515 (amide II). Analysis for $C_{40}H_{42}N_4O_3S$: calc. C, 72.92; H, 6.43; N, 8.50%; S, 4.87%; found. C, 72.71; H, 6.31; N, 8.30%; S, 4.76%.

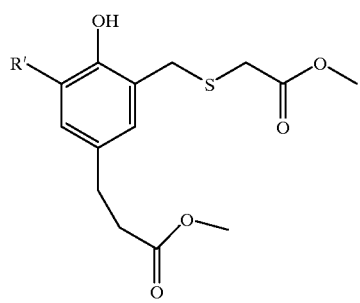

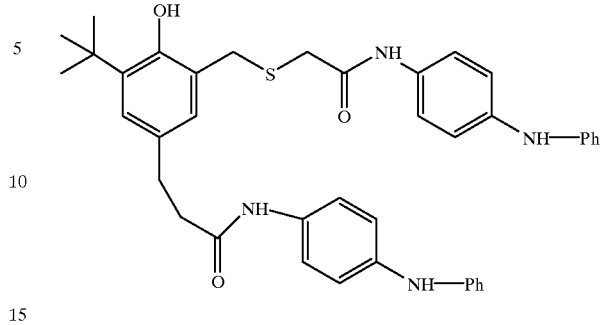

EXAMPLE A1

Incorporation Into a Rubber Substrate and Oven Ageing

Crude rubber (polybutadiene) is mixed in a Brabender mixer with sulfur, ZnO, stearic acid, the vulcanization accelerator (Vulkacit ZDBC) and (I) the compounds from Example 5 and 6 or (ii) the conventional stabilizer Vulcanox PAN. The mixture is vulcanized, and samples of the vulcanizate are treated with acetone. After drying, the residual nitrogen content is determined.

| | Values: | | |
|---|---|---|---|
| | Nitrogen content (additive) | | |
| | Before acetone treatment | After acetone treatment | |
| Additive | in ppm | in ppm | in % of initial value |
| Comp. from Example 5 | 590 | 336 | 57 |
| Comp. from Example 6 | 680 | 492 | 72 |
| Vulkanox PAN | 879 | 9 | 1 |

The different initial nitrogen values result from the different nitrogen contents of the additives.

It is found that the novel compounds are leached out to the extent of less than 55%, whereas the sample containing the conventional additive is leached out to the extent of more than 95%.

Oven ageing

After the samples have been oven aged at 100° C. for 5 weeks, the samples stabilized in accordance with the invention still have rubber elasticity and flexibility, whereas a stabilizer-free sample is brittle like glass and the sample containing PAN is hard and agile.

EXAMPLE A2

Incorporation Into Crude Rubber

Crude rubber (polybutadiene) is compounded in a tam compounder (Brabender) for 15 minutes at 150° C. und 40 rpm together with 1.5% of the additives. The rubber, in the form of 1 mm test sheets, is then extracted with acetone. The nitrogen content is measured before a nd after extraction.

Results:

| Additive | Nitrogen content | | |
|---|---|---|---|
| | before extraction ppm | after extraction in ppm | in % of initial value |
| Comp. from Example 5 | 830 | 443 | 53.4 |
| Comp. from Example 6 | 920 | 583 | 63.4 |

EXAMPLE A3

Action Under Processing Conditions

Crude rubber (polybutadiene) is compounded in a tam compounder (Brabender) at 160° C. and 60 rpm together with 0.25% of the additives until an increase in the torque/time diagram is clearly evident. The time for a 1 Nm rise is defined as the induction time and is a measure of the effectiveness of the additives in delaying oxidative crosslinking of the rubber.

Results:

| Additive | Induction time (min) |
|---|---|
| Vulkanox 4020 NA | 6.4 |
| Comp. from Example 5 | 27.4 |

EXAMPLE A4

Action Under Storage Conditions

In each case, 0.25% of the additives are mixed into the crude rubber at 60° C. on mixing rolls. 10-mm sheets are pressed out of the rubber and then aged at 80° C. in a fan-assisted oven. A sample is taken once a week and the gel content (insoluble content in toluene at 20° C.) is determined. An increasing gel content indicates oxidative crosslinking, i.e. the longer the time taken for the gel content to rise to values >1%, the better the protective action of the additive.

Results:

| Additive | Time in weeks to a gel content of >1% |
|---|---|
| Control | <2 |
| Comp. from Example 5 | >11 |
| Comp. from Example 6 | 10 |

EXAMPLE A5

Incorporation of the Additives Into Carbon Black-Filled Vulcanizates and Effectiveness After Extraction The following mixture constituents are mixed at 60° C. in a Werner & Pfleiderer LH1 Banbury-type mixer:

| | Parts by weight |
|---|---|
| Polybutadiene (Taktene 1220/Bayer) | 40.0 |
| Natural rubbers MR 5CV | 60.0 |
| Carbon black N 330 | 55.0 |
| Aromatic oil (Ingralen 450/Fuchs) | 6.0 |
| Zinc oxide | 5.0 |
| Stearic acid | 2.0 |
| Antilux 111 | 2.0 |
| Vulkanox HS | 1.5 |

The following vulcanization assistants and the additive to be tested are then admixed on the mixing rolls:

| Struktol SU 109 (75%)/sulfur preparation | 2.67 |
|---|---|
| Vulkazit MOZ | 0.6 |
| Additive | 2.5 |

From the finished mixtures, sheets with a thickness of 2 mm are vulcanized in a hot press at 150° C. for 20 minutes.

Extraction: The vulcanized sheets are extracted with acetone for 48 hours at room temperature.

Determination of the nitrogen content: The nitrogen content of the samples is determined by X-ray spectrometry before and after extraction, and the amounts originating from the additives to be tested are calculated by taking the difference between the respective values of the control (contains extractable and non-extractable nitrogen compounds from other formulation constituents, such as carbon black and accelerator).

Ageing: ISO S2 rods are stamped out of the extracted sheets, and the tensile strength and elongation at break are determined before and after ageing at 80° C.

Results:
1. Additive incorporation/nonextractable additive amounts

| Additive | Nitrogen content of the additive after extraction in % of the value before extraction. |
|---|---|
| Control | none |
| Vulkanox 4010 NA | 0 |
| Comp. from Example 5 | 50 |
| Comp. from Example 9 | 45 |
| Comp. from Example 13 | 41 |

2. Effectiveness during oven ageing at 80° C. after extraction

| Additive | Breaking strength (MPa) | | Elongation at break |
|---|---|---|---|
| | fresh | after 2 weeks | (%) after 2 weeks |
| Control | 23.2 | 6.9 | 97 |
| Vulkanox 4010 NA | 23.9 | 7.9 | 112 |
| Comp. from Example 5 | 23.7 | 13.8 | 205 |
| Comp. from Example 9 | 25.0 | 14.1 | 205 |
| Comp. from Example 13 | 23.6 | 12.5 | 195 |

What is claimed is:

1. A compound of the formula I

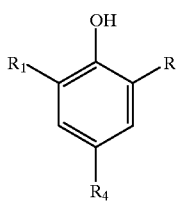

in which

R is $C_1$–$C_{18}$alkyl, $C_5$–$C_8$cycloalkyl, $C_7$–$C_9$phenylalkyl, —$CH_2$—A—$R_2$ or a group of the formula II,

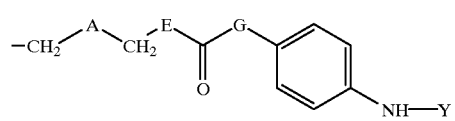

$R_1$ is $C_1$–$C_{18}$alkyl, $C_5$–$C_8$cycloalkyl, $C_7$–$C_9$phenylalkyl or a group of the formula (II), $R_2$ is $C_4$–$C_{18}$alkyl, —$(CH_2)_m$—$COOR_5$ or a group of the formula III,

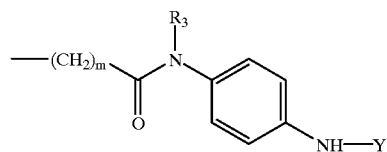

$R_3$ is hydrogen, $C_5$–$C_8$cycloalkyl or $C_1$–$C_{12}$alkyl, $R_4$ is $C_1$–$C_{18}$alkyl, $C_5$–$C_8$cycloalkyl, $C_7$–$C_9$phenylalkyl or a group of the formula II or IV

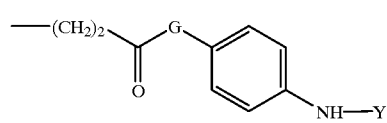

A is S or SO,

E is a direct bond, —$CH_2$—, —$CH_2$—O— or —$CH_2$—NH—,

G is —O— or —$NR_3$—,

Y is $C_1$–$C_{18}$alkyl, cyclohexyl, phenyl or alpha- or beta-naphthyl, $R_5$ is $C_1$–$C_{18}$alkyl, and m is 1 or 2, with the provisos that
either at least one of the radicals R and $R_4$ conforms to a group of the formula II or R is $CH_2$—A—$R_2$ and $R_4$ is a group of the formula IV.

2. A compound according to claim 1, in which

R is $C_1$–$C_8$alkyl, cyclohexyl, benzyl, —$CH_2$—A—$R_2$ or a group of the formula II, $R_1$ is $C_1$–$C_8$alkyl, cyclohexyl, benzyl or a group of the formula II, $R_4$ is $C_1$–$C_{12}$alkyl, cyclohexyl, benzyl or a group of the formula II, $R_2$ is $C_8$–$C_{12}$alkyl or —$(CH_2)_m$—$COOR_5$, $R_5$ is $C_8$–$C_{13}$alkyl, and E is a direct bond or —$CH_2$.

3. A compound according to claim 1, in which

R is $C_1$–$C_4$alkyl, —$CH_2$—A—$R_2$ or a group of the formula II, $R_1$ is $C_1$–$C_4$alkyl or a group of the formula II, $R_4$ is $C_1$–$C_4$alkyl or a group of the formula II or IV, $R_2$ is $C_8$–$C_{12}$alkyl, $R_3$ is hydrogen, $C_1$–$C_8$alkyl or cyclohexyl, E is a direct bond, G is $NR_3$, and Y is phenyl or alpha- or beta-naphthyl.

4. A compound according to claim 1, in which A is SO or a direct bond.

5. A compound according to claim 1, in which R is —$CH_2$—A—$R_2$, $R_1$ is $C_1$–$C_{18}$alkyl, $C_5$–$C_8$cycloalkyl or $C_7$–$C_9$ phenylalkyl and $R_4$ is a group of the formula IV.

6. A compound according to claim 1, in which R is a group of the formula II, and $R_1$ and $R_4$, independently of one another, are $C_1$–$C_{18}$alkyl, $C_5$–$C_8$cycloalkyl or $C_7$–$C_9$phenylalkyl.

7. A compound according to claim 1, in which $R_4$ is a group of the formula II, and R and $R_1$, independently of one another, are $C_1$–$C_{18}$alkyl, $C_5$–$C_8$cycloalkyl or $C_7$–$C_9$phenylalkyl sind.

8. A composition comprising an organic material which is sensitive to oxidative, thermal and/or photoinduced degradation and at least one compound of the formula I according to claim 1.

9. A composition according to claim 8, in which the organic material is an organic, preferably synthetic, polymer.

10. A composition according to claim 9, in which the organic material is an elastomer.

11. A composition according to claim 9, in which the compound of the formula I is chemically linked to the elastomer.

12. A process for stabilizing organic material which is sensitive to oxidative, thermal and/or photoinduced degradation, which comprises adding a compound of the formula I as described in claim 1 to this material.

13. A process according to claim 12, where the organic material is a polymer.

14. A process according to claim 12, where the organic material is a synthetic or natural rubber vulcanizate.

* * * * *